United States Patent
Kawasaki et al.

(10) Patent No.: US 7,166,630 B2
(45) Date of Patent: Jan. 23, 2007

(54) MAG EXPRESSION PROMOTERS

(75) Inventors: Masakazu Kawasaki, Yokohama (JP);
Nobuharu Gotoh, Tokyo (JP);
Yoshiharu Hayashi, Tokyo (JP);
Kazuyuki Kawasaki, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/969,885

(22) Filed: Oct. 22, 2004

(65) Prior Publication Data

US 2005/0090531 A1    Apr. 28, 2005

Related U.S. Application Data

(62) Division of application No. 09/979,509, filed as application No. PCT/JP00/03373 on May 25, 2000, now abandoned.

(30) Foreign Application Priority Data

May 25, 1999    (JP)    ............................. 1999-144336

(51) Int. Cl.
*A61K 31/4164*    (2006.01)

(52) U.S. Cl. ..................................................... 514/398
(58) Field of Classification Search ................. 514/415
See application file for complete search history.

(56) References Cited

FOREIGN PATENT DOCUMENTS

| | | |
|---|---|---|
| CA | 2235621 | 5/1997 |
| DE | 195 41 146 | 4/1997 |
| EP | 0 881218 | 12/1998 |

OTHER PUBLICATIONS

Mineo Tsuruta et al., "Tromboxane; Gosei Kouso Sogaizai (No. 1)", *Yakugaku Zasshi*, vol. 109, No. 1, pp. 33-45 (1989).

Andrew P. Mizisin et al., "Myelin splitting, Schwann cell injury and demyelination in feline diabetic neuropathy", Acta Neuropathol, 95, pp. 171-174, 1998.

G. Said et al., "Uncommon early-onset neuropathy in diabetic patients", Journal of Neurology, vol. 245, No. 2, pp. 61-68, XP002299181, Feb. 1998.

*Primary Examiner*—Phyllis G. Spivack
(74) *Attorney, Agent, or Firm*—Wenderoth, Lind & Ponack, L.L.P.

(57) ABSTRACT

A method for promoting myelination of an axon comprising administering 4-[α-hydroxy-5-(1-imidazolyl)-2-methylbenzyl]-3,5-dimethylbenzoic acid is disclosed.

2 Claims, 3 Drawing Sheets

V: DMSO, A: ascorbic acid (50 μg/ml)

Effect of compound of invention on MAG expression in cultured cell

Time-course changes in MAG expression after addition of compound of invention

MAG EXPRESSION PROMOTERS

This application is a Divisional application of Ser. No. 09/979,509, filed Mar. 5, 2002, now abandoned which is a 371 of PCT/JP00/03373, filed May 25, 2000.

TECHNICAL FIELD

This invention relates to MAG expression promoters. Specifically, the present invention relates to MAG expression promoters useful as an agent for the prophylaxis and/or treatment of diseases mainly presenting hypomyelination, and further, dysmyelination or demyelination. More particularly, the present invention relates to MAG expression promoters containing 4-[α-hydroxy-5-(1-imidazolyl)-2-methylbenzyl]-3,5-dimethylbenzoic acid, its optically active form or its pharmaceutically acceptable salt as an active ingredient.

BACKGROUND ART

Vertebrata have developed myelinated nerve to enable high speed processing of a large amount of information. The myelin sheath, which is characteristic of the myelinated nerve, is formed upon enveloping of nerve axon by cytoplasmic membrane of oligodendrocyte or Schwann cell, and has a multilayer structure. As a result, the nerve becomes insulated as well as acquires an extremely high impedance and extremely low capacitance. The sodium channels are present in accumulation in the nodes of Ranvier, which is a cut line between a myelin sheath and another myelin sheath, and facilitate saltatory conduction of an impulse and enable high speed processing of information (namely, high nerve conduction velocity).

The main component forming the myelin sheath is myelin and, as a component to stabilize the multilayer structure of the myelin sheath, myelin specific proteins are known. Of these, proteolipid protein and $P_0$ protein are involved in crosslinking and adhesion between myelin membranes, and myelin basic protein (hereinafter to be referred to as MBP) is present in the cytoplasm of myelin sheath and involved in compaction of the sheath (Morell P. et al., in Basic Neurochemistry, Siegel G J et al. Eds. Ravan Press, p. 117–143 (1994)). In addition, myelin-associated glycoprotein (hereinafter sometimes to be referred to as MAG) is involved in adhesion between axon and myelin sheath (Quarles R H, Myelin-associated glycoprotein: functional and clinical aspects, in Neuronal and Glial Proteins: Structure, Function and Clinical Application, Marangos P J et al. Eds. Academic Press, New York, p. 295 (1988)).

The MAG belongs to the immunoglobulin superfamily and the electrophoretic mobility is 100-kDa. When myelination is started, MAG is expressed by the oligodendrocyte in the central nervous system and by Schwann cell in the peripheral nervous system. The proportion of MAG in myelin is only 1% in the central nervous system and 0.1% in the peripheral nervous system. Recently, it has been clarified that MAG plays not only a role as a simple adhesion molecule but is also positively involved in the formation and maintenance of myelin sheath, as mentioned below.

In Schwann cell, where MAG is excessively expressed in vitro, myelination is promoted (Owens G C et al., J. Cell Biol., 111, p. 1171–1182 (1990)), but in Schwann cell, where expression of MAG is decreased, myelination is suppressed (Owens G C et al., Neuron, 7, p. 565–575 (1991)). In vivo, the number of myelinated nerves of MAG deficient mice decreases and the number of unmyelinated nerve increases, which is considered to be caused by a retardation in the myelin formation (Bartsch S. et al., Brain Res. 762, p. 231–234 (1997)). On the other hand, there is also a report documenting that, despite a morphological abnormality observed in the periaxonal space between axon and myelin sheath, no difference is found in the number of myelinated nerves, thickness of myelin sheath or the diameter of axon, of the normal mice and MAG deficient mice (Li C. et al. Nature, 369, p. 747–750 (1994)). Therefore, many points remain unknown about the relationship between MAG and myelination.

As regards the molecular mechanism of myelination, there is only a report at present that MAG binds with an axon receptor to activate Fyn tyrosine kinase (Umemori H. et al., Nature, 367, p. 572–576 (1994)), and then promotes expression of MBP gene (Umemori H., J. Neurosci., 19, p. 1393–1397 (1999)), which is not sufficient to clarify the mechanism.

As the diseases mainly presenting hypomyelination, and further, dysmyelination or demyelination, multiple sclerosis, encephalitis, myelitis, Guillain-Barrè syndrome, chronic inflammatory demyelinating polyradiculitis, heavy metal toxicosis, diphtheria toxicosis, hypothyroidism, metachromatic leukodegeneration, Charcot-Marie-Tooth disease and the like are known (Takeshi Yasuda et al., Clinical Test, 40, p. 760–766 (1996)).

These diseases are reported to be treated with interferon, steroid, γ-globulin, plasma exchange or immunosuppressant (Gen Sobue, Brain and Development, 30, p. 115–120 (1998), Hajime Harukawa et al., Nippon Rinsho, 55, p. 187–194 (1997)), but the situation is not entirely satisfactory. Since in patients with multiple sclerosis, disappearance of MAG in the early stages of onset of the disease is observed (Moller J R, Ann. Neurol., 22, p. 469–474 (1987)), a drug that promotes expression of MAG is expected to be effective for the prophylaxis and/or treatment of the onset of the above-mentioned diseases.

In JP-A-60-34952, JP-B-64-7074, JP-B-3-16348, JP-B-4-15781, JP-B-4-15782, JP-B-5-29031, JP-B-5-41143 and JP-B-5-74589, the compound of the formula (I) to be mentioned below is disclosed, which is useful for the prophylaxis and treatment of thrombosis, stroke, myocardial infarction, sudden cardiac death, angina pectoris, hypertension, asthma, nephritis and the like, optically active forms thereof and pharmaceutically acceptable salts thereof having a pharmacological action, such as potent $TXA_2$ biosynthesis inhibitory action, platelet aggregation inhibitory action and vasodilating action and the like. WO97/24333 discloses that, of these compounds, 4-[α-hydroxy-5-(1-imidazolyl)-2-methylbenzyl]-3,5-dimethylbenzoic acid, optically active forms thereof and pharmaceutically acceptable salts thereof are useful agents for the prophylaxis and/or treatment of diabetic complications.

However, it is not described or suggested that a compound of the formula (I) to be mentioned later has an action to promote expression of MAG.

It is an object of the present invention to provide MAG expression promoters. More particularly, an object of the present invention is to provide MAG expression promoters that can be an agent for the prophylaxis and/or treatment of diseases mainly presenting hypomyelination, and further, dysmyelination or demyelination.

DISCLOSURE OF THE INVENTION

The present inventors have conducted intensive studies and found that a compound of the following formula (I), an optically active form thereof and a pharmaceutically acceptable salt thereof promote expression of MAG, and that they are useful as an agent for the prophylaxis and/or treatment of the diseases mainly presenting hypomyelination, and further, dysmyelination or demyelination, which resulted in the completion of the following invention.

(1) A MAG expression promoter containing a compound of the formula (I)

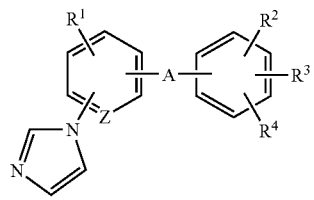
(I)

wherein
$R^1$ is a hydrogen atom, a halogen atom, an alkyl group or an alkoxy group;
$R^2$ and $R^3$ are the same or different and each is a hydrogen atom or an alkyl group;
$R^4$ is an alkyl group, —COOH, —COOR$^5$, —CONR$^6$R$^7$, —CH$_2$NR$^6$R$^7$, —CH$_2$OH or —CH$_2$OR$^8$;
wherein $R^5$ and $R^8$ are each an alkyl group, and $R^6$ and $R^7$ are the same or different and each is a hydrogen atom or an alkyl group, or $R^6$ and $R^7$ in combination form imidazole together with the adjacent nitrogen atom;
A is —CH(OH)—, —C(=O)— or —CH$_2$—; and
Z is =CH— or =N—, an optically active form thereof or a pharmaceutically acceptable salt thereof (hereinafter sometimes to be generally referred to as the compound of the present invention).

(2) The MAG expression promoter of the above-mentioned (1), which is applicable to a disease of mammals inclusive of humans, caused by hypomyelination.

(3) The MAG expression promoter of the above-mentioned (1), which is applicable to a disease of mammals inclusive of humans, the disease mainly presents dysmyelination or demyelination.

(4) The MAG expression promoter of the above-mentioned (1), which is applicable to a disease of mammals inclusive of humans, the disease being multiple sclerosis, encephalitis, myelitis, Guillain-Barrè syndrome, chronic inflammatory demyelinating polyradiculitis, heavy metal toxicosis, diphtheria toxicosis, hypothyroidism, metachromatic leukodegeneration or Charcot-Marie-Tooth disease.

(5) The MAG expression promoter of any of the above-mentioned (1) to (4), wherein, in the formula (I), $R^1$ is a halogen atom, an alkyl group or an alkoxy group.

(6) A MAG expression promoter comprising 4-[α-hydroxy-5-(1-imidazolyl)-2-methylbenzyl]-3,5-dimethylbenzoic acid, an optically active form thereof or a pharmaceutically acceptable salt thereof.

(7) A method of promoting expression of MAG, which method comprises administering a compound of the formula (I)

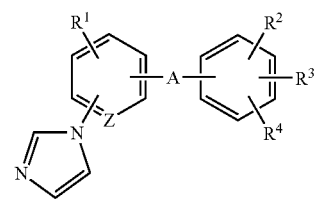
(I)

wherein
$R^1$ is a hydrogen atom, a halogen atom, an alkyl group or an alkoxy group;
$R^2$ and $R^3$ are the same or different and each is a hydrogen atom or an alkyl group;
$R^4$ is an alkyl group, —COOH, —COOR$^5$, —CONR$^6$R$^7$, —CH$_2$NR$^6$R$^7$, —CH$_2$OH or —CH$_2$OR$^8$;
wherein $R^5$ and $R^8$ are each an alkyl group, and $R^6$ and $R^7$ are the same or different and each is a hydrogen atom or an alkyl group, or $R^6$ and $R^7$ in combination form imidazole together with the adjacent nitrogen atom;
A is —CH(OH)—, —C(=O)— or —CH$_2$—; and
Z is =CH— or =N—, an optically active form thereof or a pharmaceutically acceptable salt thereof to mammals inclusive of humans.

(8) The method of the above-mentioned (7), wherein, in the formula (I), $R^1$ is a halogen atom, an alkyl group or an alkoxy group.

(9) A method for promoting expression of MAG, which method comprises administering 4-[α-hydroxy-5-(1-imidazolyl)-2-methylbenzyl]-3,5-dimethylbenzoic acid, an optically active form thereof or a pharmaceutically acceptable salt thereof to mammals inclusive of humans.

(10) A method for prophylaxis and/or therapy of a disease caused by hypomyelination, which method comprises administering a compound of the formula (I)

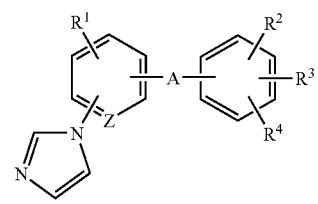
(I)

wherein
$R^1$ is a hydrogen atom, a halogen atom, an alkyl group or an alkoxy group;
$R^2$ and $R^3$ are the same or different and each is a hydrogen atom or an alkyl group;
$R^4$ is an alkyl group, —COOH, —COOR$^5$, —CONR$^6$R$^7$, —CH$_2$NR$^6$R$^7$, —CH$_2$OH or —CH$_2$OR$^8$;
wherein $R^5$ and $R^6$ are each an alkyl group, and $R^8$ and $R^7$ are the same or different and each is a hydrogen atom or an alkyl group, or $R^6$ and $R^7$ in combination form imidazole together with the adjacent nitrogen atom;

A is —CH(OH)—, —C(=O)— or —CH$_2$—; and

Z is =CH— or =N—, an optically active form thereof or a pharmaceutically acceptable salt thereof to mammals inclusive of humans.

(11) The method of the above-mentioned (10), wherein, in the formula (I), R$^1$ is a halogen atom, an alkyl group or an alkoxy group.

(12) A method for prophylaxis and/or therapy of a disease caused by hypomyelination, which method comprises administering 4-[α-hydroxy-5-(1-imidazolyl)-2-methylbenzyl]-3,5-dimethylbenzoic acid, an optically active form thereof or a pharmaceutically acceptable salt thereof to mammals inclusive of humans.

(13) A method for prophylaxis and/or therapy of a disease mainly presenting dysmyelination or demyelination, which method comprises administering a compound of the formula (I)

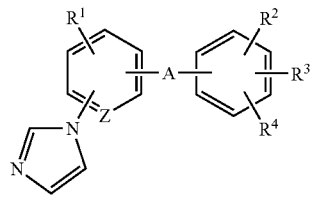

(I)

wherein

R$^1$ is a hydrogen atom, a halogen atom, an alkyl group or an alkoxy group;

R$^2$ and R$^3$ are the same or different and each is a hydrogen atom or an alkyl group;

R$^4$ is an alkyl group, —COOH, —COOR$^5$, —CONR$^6$R$^7$, —CH$_2$NR$^6$R$^7$, —CH$_2$OH or —CH$_2$OR$^8$;

wherein R$^5$ and R$^8$ are each an alkyl group, and R$^6$ and R$^7$ are the same or different and each is a hydrogen atom or an alkyl group, or R$^6$ and R$^7$ in combination form imidazole together with the adjacent nitrogen atom;

A is —CH(OH)—, —C(=O)— or —CH$_2$—; and

Z is =CH— or =N—, an optically active form thereof or a pharmaceutically acceptable salt thereof to mammals inclusive of humans.

(14) The method of the above-mentioned (13), wherein, in the formula (I), R$^1$ is a halogen atom, an alkyl group or an alkoxy group.

(15) A method for prophylaxis and/or therapy of a disease mainly presenting dysmyelination or demyelination, which method comprises administering 4-[α-hydroxy-5-(1-imidazolyl)-2-methylbenzyl]-3,5-dimethylbenzoic acid, an optically active form thereof or a pharmaceutically acceptable salt thereof to mammals inclusive of humans.

(16) A method for prophylaxis and/or therapy of multiple sclerosis, encephalitis, myelitis, Guillain-Barrè syndrome, chronic inflammatory demyelinating polyradiculitis, heavy metal toxicosis, diphtheria toxicosis, hypothyroidism, metachromatic leukodegeneration or Charcot-Marie-Tooth disease, which method comprises administering a compound of the formula (I)

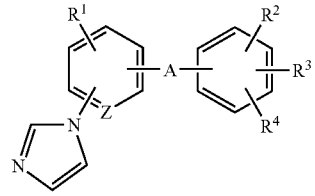

(I)

wherein

R$^1$ is a hydrogen atom, a halogen atom, an alkyl group or an alkoxy group;

R$^2$ and R$^3$ are the same or different and each is a hydrogen atom or an alkyl group;

R$^4$ is an alkyl group, —COOH, —COOR$^5$, —CONR$^6$R$^7$, —CH$_2$NR$^6$R$^7$, —CH$_2$OH or —CH$_2$OR$^8$;

wherein R$^5$ and R$^8$ are each an alkyl group, and R$^6$ and R$^7$ are the same or different and each is a hydrogen atom or an alkyl group, or R$^6$ and R$^7$ in combination form imidazole together with the adjacent nitrogen atom;

A is —CH(OH)—, —C(=O)— or —CH$_2$—; and

Z is =CH— or =N—, an optically active form thereof or a pharmaceutically acceptable salt thereof to mammals inclusive of humans.

(17) The method of the above-mentioned (16), wherein, in the formula (I), R$^1$ is a halogen atom, an alkyl group or an alkoxy group.

(18) A method for prophylaxis and/or therapy of multiple sclerosis, encephalitis, myelitis, Guillain-Barrè syndrome, chronic inflammatory demyelinating polyradiculitis, heavy metal toxicosis, diphtheria toxicosis, hypothyroidism, metachromatic leukodegeneration or Charcot-Marie-Tooth disease, which method comprises administering 4-[α-hydroxy-5-(1-imidazolyl)-2-methylbenzyl]-3,5-dimethylbenzoic acid, an optically active form thereof or a pharmaceutically acceptable salt thereof to mammals inclusive of humans.

(19) Use of a compound of the formula (I)

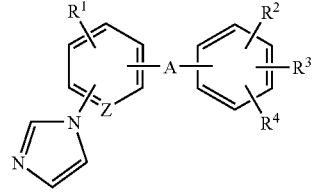

(I)

wherein

R$^1$ is a hydrogen atom, a halogen atom, an alkyl group or an alkoxy group;

R$^2$ and R$^3$ are the same or different and each is a hydrogen atom or an alkyl group;

R$^4$ is an alkyl group, —COOH, —COOR$^5$, —CONR$^6$R$^7$, —CH$_2$NR$^6$R$^7$, —CH$_2$OH or —CH$_2$OR$^8$;

wherein R$^5$ and R$^8$ are each an alkyl group, and R$^6$ and R$^7$ are the same or different and each is a hydrogen atom or an alkyl group, or R$^6$ and R$^7$ in combination form imidazole together with the adjacent nitrogen atom;

A is —CH(OH)—, —C(=O)— or —CH$_2$—; and
Z is =CH— or =N—, an optically active form thereof or a pharmaceutically acceptable salt thereof for producing a MAG expression promoter.

(20) The use of the above-mentioned (19), wherein, in the formula (I), R$^1$ is a halogen atom, an alkyl group or an alkoxy group.

(21) Use of 4-[α-hydroxy-5-(1-imidazolyl)-2-methylbenzyl]-3,5-dimethylbenzoic acid, an optically active form thereof or a pharmaceutically acceptable salt thereof for producing a MAG expression promoter.

(22) Use of a compound of the formula (I)

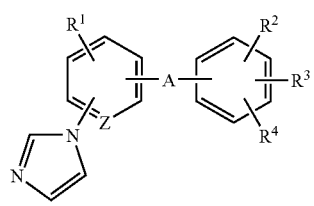

wherein
R$^1$ is a hydrogen atom, a halogen atom, an alkyl group or an alkoxy group;
R$^2$ and R$^3$ are the same or different and each is a hydrogen atom or an alkyl group;
R$^4$ is an alkyl group, —COOH, —COOR$^5$, —CONR$^6$R$^7$, —CH$_2$NR$^6$R$^7$, —CH$_2$OH or —CH$_2$OR$^8$;
  wherein R$^5$ and R$^8$ are each an alkyl group, and R$^6$ and R$^7$ are the same or different and each is a hydrogen atom or an alkyl group, or R$^6$ and R$^7$ in combination form imidazole together with the adjacent nitrogen atom;
A is —CH(OH)—, —C(=O)— or —CH$_2$—; and
Z is =CH— or =N—, an optically active form thereof or a pharmaceutically acceptable salt thereof for producing a MAG expression promoter applicable to a disease in mammals inclusive of humans, which is caused by hypomyelination.

(23) The use of the above-mentioned (22), wherein, in the formula (I), R$^1$ is a halogen atom, an alkyl group or an alkoxy group.

(24) Use of 4-[α-hydroxy-5-(1-imidazolyl)-2-methylbenzyl]-3,5-dimethylbenzoic acid, an optically active form thereof or a pharmaceutically acceptable salt thereof for producing a MAG expression promoter applicable to a disease in mammals inclusive of humans, which is caused by hypomyelination.

(25) Use of a compound of the formula (I)

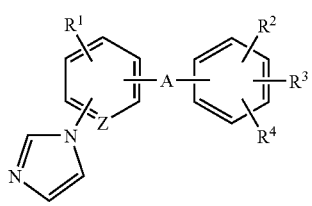

wherein
R$^1$ is a hydrogen atom, a halogen atom, an alkyl group or an alkoxy group;
R$^2$ and R$^3$ are the same or different and each is a hydrogen atom or an alkyl group;
R$^4$ is an alkyl group, —COOH, —COOR$^5$, —CONR$^6$R$^7$, —CH$_2$NR$^6$R$^7$, —CH$_2$OH or —CH$_2$OR$^8$;
  wherein R$^5$ and R$^8$ are each an alkyl group, and R$^6$ and R$^7$ are the same or different and each is a hydrogen atom or an alkyl group, or R$^6$ and R$^7$ in combination form imidazole together with the adjacent nitrogen atom;
A is —CH(OH)—, —C(=O)— or —CH$_2$—; and
Z is =CH— or =N—, an optically active form thereof or a pharmaceutically acceptable salt thereof for producing a MAG expression promoter applicable to a disease in mammals inclusive of humans, which mainly presents dysmyelination or demyelination.

(26) The use of the above-mentioned (25), wherein, in the formula (I), R$^1$ is a halogen atom, an alkyl group or an alkoxy group.

(27) Use of 4-[α-hydroxy-5-(1-imidazolyl)-2-methylbenzyl]-3,5-dimethylbenzoic acid, an optically active form thereof or a pharmaceutically acceptable salt thereof for producing a MAG expression promoter applicable to a disease in mammals inclusive of humans, which mainly presents dysmyelination or demyelination.

(28) Use of a compound of the formula (I)

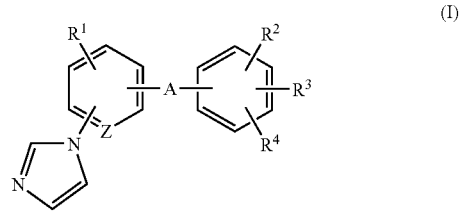

wherein
R$^1$ is a hydrogen atom, a halogen atom, an alkyl group or an alkoxy group;
R$^2$ and R$^3$ are the same or different and each is a hydrogen atom or an alkyl group;
R$^4$ is an alkyl group, —COOH, —COOR$^5$, —CONR$^6$R$^7$, —CH$_2$NR$^6$R$^7$, —CH$_2$OH or —CH$_2$OR$^8$;
  wherein R$^5$ and R$^8$ are each an alkyl group, and R$^6$ and R$^7$ are the same or different and each is a hydrogen atom or an alkyl group, or R$^6$ and R$^7$ in combination form imidazole together with the adjacent nitrogen atom;
A is —CH(OH)—, —C(=O)— or —CH$_2$—; and
Z is =CH— or =N—, an optically active form thereof or a pharmaceutically acceptable salt thereof for producing a MAG expression promoter applicable to a disease in mammals inclusive of humans, which is multiple sclerosis, encephalitis, myelitis, Guillain-Barrè syndrome, chronic inflammatory demyelinating polyradiculitis, heavy metal toxicosis, diphtheria toxicosis, hypothyroidism, metachromatic leukodegeneration or Charcot-Marie-Tooth disease.

(29) The use of the above-mentioned (28), wherein, in the formula (I), $R^1$ is a halogen atom, an alkyl group or an alkoxy group.

(30) Use of 4-[α-hydroxy-5-(1-imidazolyl)-2-methylbenzyl]-3,5-dimethylbenzoic acid, an optically active form thereof or a pharmaceutically acceptable salt thereof for producing a MAG expression promoter applicable to a disease in mammals inclusive of humans, which is multiple sclerosis, encephalitis, myelitis, Guillain-Barrè syndrome, chronic inflammatory demyelinating polyradiculitis, heavy metal toxicosis, diphtheria toxicosis, hypothyroidism, metachromatic leukodegeneration or Charcot-Marie-Tooth disease.

(31) A commercial package comprising a MAG expression promoter comprising a compound of the formula (I)

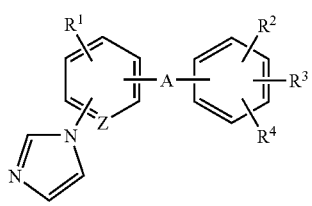

wherein $R^1$ is a hydrogen atom, a halogen atom, an alkyl group or an alkoxy group;

$R^2$ and $R^3$ are the same or different and each is a hydrogen atom or an alkyl group;

$R^4$ is an alkyl group, —COOH, —COOR$^5$, —CONR$^6$R$^7$, —CH$_2$NR$^6$R$^7$, —CH$_2$OH or —CH$_2$OR$^8$;

wherein $R^5$ and $R^8$ are each an alkyl group, and $R^8$ and $R^7$ are the same or different and each is a hydrogen atom or an alkyl group, or $R^6$ and $R^7$ in combination form imidazole together with the adjacent nitrogen atom;

A is —CH(OH)—, —C(=O)— or —CH$_2$—; and

Z is =CH— or =N—, an optically active form thereof or a pharmaceutically acceptable salt thereof and a written matter associated therewith, the written matter stating that the MAG expression promoter can or should be used for promoting expression of MAG.

(32) The commercial package of the above-mentioned (31), wherein, in the formula (I), $R^1$ is a halogen atom, an alkyl group or an alkoxy group.

(33) A commercial package comprising a MAG expression promoter comprising 4-[α-hydroxy-5-(1-imidazolyl)-2-methylbenzyl]-3,5-dimethylbenzoic acid, an optically active form thereof or a pharmaceutically acceptable salt thereof and a written matter associated therewith, the written matter stating that the MAG expression promoter can or should be used for promoting expression of MAG.

BRIEF DESCRIPTION OF DRAWINGS

FIG. 1, FIG. 2 and FIG. 3 are microscopic photographs showing the results of Experimental Example 1, wherein FIG. 1 shows the effect of a negative control compound (DMSO) on myelination of axon.

FIG. 2 is a microscopic photograph showing the effect of a positive control compound (ascorbic acid) on myelination of axon.

FIG. 3 is a microscopic photograph showing the effect of the compound of the present invention (Y-128 to be mentioned later) on myelination of axon.

EMBODIMENT OF INVENTION

Figure 1:
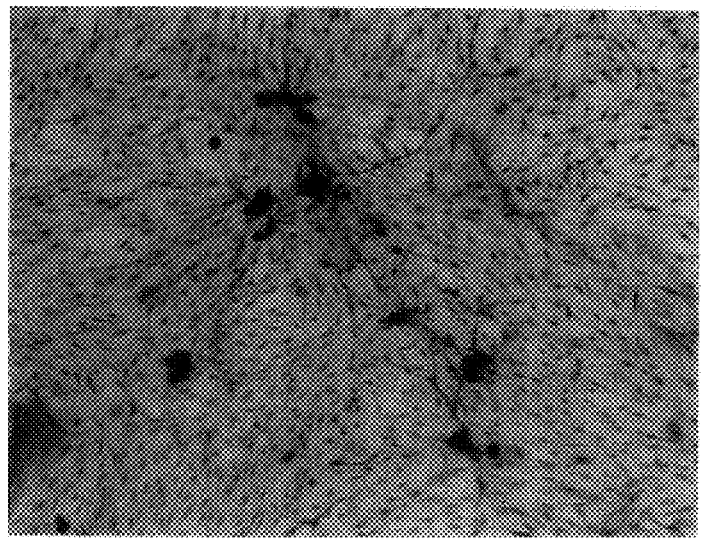

The MAG expression promoter of the present invention encompasses any such promoter as long as it can promote in vitro or in vivo expression of MAG at a gene level or a protein level.

The disease caused by hypomyelination is a disease of mammals inclusive of humans, including any disease mainly presenting the disease state of hypomyelination, dysmyelination or demyelination.

Moreover, the disease mainly presenting dysmyelination or demyelination means diseases of mammals inclusive of humans, and encompasses any disease mainly presenting the disease state of hypomyelination, dysmyelination or demyelination. Examples thereof include multiple sclerosis, encephalitis, myelitis, Guillain-Barrè syndrome, chronic inflammatory demyelinating polyradiculitis, heavy metal toxicosis, diphtheria toxicosis, hypothyroidism, metachromatic leukodegeneration, Charcot-Marie-Tooth disease and the like.

In the present specification, the definition of each symbol in the formula (I) is as follows.

The halogen atom at $R^1$ may be chlorine atom, bromine atom, fluorine atom and iodine atom, with preference given to chlorine atom.

The alkyl group at $R^1$, $R^2$, $R^3$, $R^4$, $R^5$, $R^6$, $R^7$ and $R^8$ is a linear or branched chain alkyl group having 1 to 10 carbon atoms, such as methyl, ethyl, propyl, isopropyl, butyl, isobutyl, sec-butyl, tert-butyl, pentyl, hexyl, heptyl, octyl, nonyl, decyl and the like, with preference given to an alkyl group having 1 to 4 carbon atoms.

The alkoxy group at $R^1$ is linear or branched chain alkoxy group having 1 to 6 carbon atoms, such as methoxy, ethoxy, propoxy, isopropoxy, butoxy, isobutoxy, sec-butoxy, tert-butoxy, pentyloxy, hexyloxy and the like.

The compound of the present invention can be synthesized according to a method described in JP-A-60-34952, JP-B-64-7074, JP-B-3-16348, JP-B-4-15781, JP-B-4-15782, JP-B-5-29031, JP-B-5-41143 and JP-B-5-74589.

An optically active form of the compound of the present invention can be produced by a conventional method, such as racemic resolution and the like.

A pharmaceutically acceptable salt of the compound of the present invention is exemplified by acid addition salts with inorganic acid, such as hydrochloric acid, hydrobromic acid, sulfuric acid and the like, or organic acids, such as fumaric acid, maleic acid, mandelic acid, citric acid, tartaric acid, salicylic acid and the like, salts with a metal such as sodium, potassium, calcium, magnesium, aluminum and the like, and salts with amino acid such as lysine and the like. In addition, 1/2 hydrate, 1/3 hydrate, 2/3 hydrate, monohydrate, 3/2 hydrate, dihydrate and the like thereof are also encompassed. Salts of these can be produced by a conventional method.

The compound of the present invention can be used as an active ingredient of a MAG expression promoter for promoting the expression of MAG in mammals such as a human, cow, horse, dog, mouse, rat and the like. Therefore, the compound of the present invention is useful as an agent for the prophylaxis and/or treatment of diseases mainly presenting hypomyelination, further, dysmyelination or demyelination, particularly as an agent for the prophylaxis and/or treatment of multiple sclerosis, encephalitis, myelitis, Guillain-Barre syndrome, chronic inflammatory demyelinating polyradiculitis, heavy metal toxicosis, diphtheria toxicosis, hypothyroidism, metachromatic leukodegeneration and Charcot-Marie-Tooth disease.

Of the compounds of the present invention, preferable compounds are as follows.

(1) 2-(1-imidazolyl)-α-(2,4,6-trimethylphenyl)-benzenemethanol
(2) 2-(1-imidazolyl)-2',4',6'-trimethylbenzophenone
(3) 4-(1-imidazolyl)-α-(2,4,6-trimethylphenyl)-benzenemethanol
(4) 3-chloro-4-(1-imidazolyl)-α-(2,4,6-trimethylphenyl) benzenemethanol
(5) 3-(1-imidazolyl)-α-(2,4,6-trimethylphenyl)-benzenemethanol
(6) 2-chloro-5-(1-imidazolyl)-α-(2,4,6-trimethylphenyl) benzenemethanol
(7) 5-(1-imidazolyl)-2-methyl-α-(2,4,6-trimethylphenyl) benzenemethanol and its monohydrochloride
(8) 5-(1-imidazolyl)-2-methoxy-α-(2,4,6-trimethylphenyl) benzenemethanol
(9) 5-(1-imidazolyl)-2-methyl-α-(4-hydroxymethyl-2,6-dimethylphenyl)benzenemethanol
(10) 2-chloro-5-(1-imidazolyl)-α-(4-hydroxymethyl-2,6-dimethylphenyl)benzenemethanol
(11) 5-(1-imidazolyl)-2-methyl-α-(4-methoxymethyl-2,6-dimethylphenyl)benzenemethanol
(12) 4-[α-hydroxy-5-(1-imidazolyl)-2-methylbenzyl]-3,5-dimethylbenzoic acid and its sodium salt 1/2 hydrate
(13) methyl 4-[α-hydroxy-5-(1-imidazolyl)-2-methylbenzyl]-3,5-dimethylbenzoate
(14) 5-(1-imidazolyl)-2,2',6'-trimethyl-4'-(1-imidazolylmethyl)benzophenone
(15) ethyl 4-[α-hydroxy-5-(1-imidazolyl)-2-methylbenzyl]-3,5-dimethylbenzoate
(16) N-methyl 4-[α-hydroxy-5-(1-imidazolyl)-2-methylbenzyl]-3,5-dimethylbenzamide
(17) 4-[α-hydroxy-2-chloro-5-(1-imidazolyl)benzyl]-3,5-dimethylbenzoic acid
(18) 4-[α-hydroxy-5-(1-imidazolyl)-2-methoxybenzyl]-3,5-dimethylbenzoic acid
(19) (S)-4-[α-hydroxy-5-(1-imidazolyl)-2-methylbenzyl]-3,5-dimethylbenzoic acid (hereinafter sometimes to be referred to as Y-128)
(20) 4-[5-(1-imidazolyl)-2-methylbenzyl]-3,5-dimethylbenzoic acid
(21) methyl (S)-4-[α-hydroxy-5-(1-imidazolyl)-2-methylbenzyl]-3,5-dimethylbenzoate
(22) α-[2-(1-imidazolyl)pyridin-5-yl]-2,4,6-trimethylbenzenemethanol The MAG expression promoter of the present invention is formulated as a typical pharmaceutical composition or a pharmaceutical preparation and administered orally or parenterally. For example, the ompound of the present invention and a pharmaceutically acceptable carrier (e.g., excipient, binder, disintegrant, corrigent, flavor, emulsifier, diluent, solubilizer etc.) are mixed to give a pharmaceutical composition or a pharmaceutical preparation in a suitable form for oral or parenteral administration. The pharmaceutical preparation includes solid preparation, semi-solid preparation and liquid preparation. Examples thereof include tablet, pill, powder, granule, capsule, troche, syrup, solution, emulsion, suspension, injection (liquid, suspension etc.), suppository, inhalant, percutaneously absorbable drug, eye drop, eye ointment and the like.

When a solid preparation is produced, additives are used. Examples of the additive include sucrose, lactose, cellulose, D-mannitol, maltitol, dextran, starch, agar, alginate, chitin, chitosan, pectin, gum tragacanth, gum arabic, gelatin, collagen, casein, albumin, calcium phosphate, sorbitol, glycine, carboxy methylcellulose, polyvinylpyrrolidone, hydroxypropylcellulose, hydroxypropylmethylcellulose, glycerin, polyethylene glycol, sodium hydrogencarbonate, magnesium stearate, talc and the like. Tablets can be prepared into those applied with general coating as necessary, such as sugar-coated tablets, enteric coated tablets and film coated tablets. Moreover, two-layer tablets and multi-layer tablets can be prepared.

When a semi-solid preparation is produced, plant and animal fats and oils (olive oil, corn oil, castor oil etc.), mineral fats and oils (petrolatum, white petrolatum, solid paraffin etc.), waxes (jojoba oil, carnauba wax, bees wax etc.), partially synthesized or entirely synthesized glycerin fatty acid ester (lauric acid, myristic acid or palmitic acid glyceride etc.) and the like can be used. Examples of commercially available products of these include Witepsol (manufactured by Dynamitnovel Ltd.), Farmazol (NOF Corporation) and the like.

When a liquid preparation is produced, additives are used. For example, sodium chloride, sorbitol, glycerin, olive oil, propylene glycol, ethyl alcohol and the like are used. Particularly, when an injection is produced, a sterile aqueous solution (e.g., physiological saline), an isotonic solution or an oily solution (e.g., sesame oil, soybean oil) is used. Where necessary, a suitable suspending agent (e.g., sodium carboxymethylcellulose), nonionic surfactant, solubilizer (e.g., benzyl benzoate, benzyl alcohol) and the like can be concurrently used. When an eye drop is produced, an aqueous liquid or aqueous solution is used. Particularly, sterile aqueous solution for injection is used. An eye drop may contain various additives, such as buffer, isotonicity agent, solubilizer, preservative, viscosity agent, chelating agent, pH adjusting agent and aromatic as necessary. As the buffer, borate buffer, acetate buffer, carbonate buffer and the like are preferable for reducing stimulation. The pH is preferably adjusted to generally about 6–8.5.

The content of the compound of the present invention in a pharmaceutical composition or pharmaceutical preparation is 0.1–100 wt % of the pharmaceutical composition or pharmaceutical preparation, which is suitably 1–50 wt %. While the dose varies depending on the symptom, body weight, age and the like of patients, it is generally about 0.01–100 mg/kg by oral administration for an adult per day, which is preferably administered once or several times a day. For administration, oral, rectal and parenteral (e.g., muscular, intravenous, percutaneous and subcutaneous) administrations are employed.

EXAMPLES

The present invention is explained in detail in the following by referring to Formulation Examples and Experimental Examples. These do not limit the present invention in any way.

| Formulation Example 1: film-coated tablet | |
|---|---|
| Y-128 | 50.0 mg |
| D-mannitol | 70.5 mg |
| cornstarch | 16.0 mg |
| sodium hydrogencarbonate | 15.0 mg |
| hydroxypropylmethylcellulose | 3.0 mg |
| talc | 5.0 mg |
| magnesium stearate | 0.5 mg |

Y-128, D-mannitol, cornstarch and sodium hydrogencarbonate were mixed and the mixture was applied to fluidized granulation while spraying an aqueous solution of hydroxypropylmethylcellulose. The granulate was passed through a 24 mesh sieve, and talc and magnesium stearate were added. Using a rotary tablet press (Kikusui Seisakusho Ltd.), tablets weighing 160 mg per tablet were produced. Then, using hydroxypropylmethylcellulose as a film coating base, 6 mg of coating per tablet was applied to give film-coated tablets.

| Formulation Example 2: fine granules | |
|---|---|
| Y-128 | 10% |
| D-mannitol | 89.5% |
| hydroxypropylcellulose | 0.5% |

Y-128 and D-mannitol were mixed and an aqueous solution of hydroxypropylcellulose was added. The mixture was kneaded, granulated and dried at 50° C. The granulate was passed through a 32 mesh sieve to give fine granules.

| Formulation Example 3: tablet | |
|---|---|
| Y-128 | 50.0 mg |
| D-mannitol | 30.0 mg |
| cornstarch | 19.0 mg |
| sodium hydrogencarbonate | 15.0 mg |
| hydroxypropylmethylcellulose | 1.5 mg |
| talc | 4.0 mg |
| magnesium stearate | 0.5 mg |

Y-128, D-mannitol, cornstarch and sodium hydrogencarbonate were mixed and the mixture was applied to fluidized granulation while spraying an aqueous solution of hydroxypropylmethylcellulose. The granulate was passed through a 24 mesh sieve, and talc and magnesium stearate were added. Using a rotary tablet press (Kikusui Seisakusho Ltd.), tablets weighing 120 mg per tablet were produced.

| Formulation Example 4: fine granules | |
|---|---|
| Y-128 | 5% |
| D-mannitol | 92% |
| hydroxypropylmethylcellulose | 3% |

Y-128 and D-mannitol were mixed and an aqueous solution of hydroxypropylmethylcellulose was added. The mixture was kneaded, granulated and dried at 50° C. The granulate was passed through a 32 mesh sieve to give fine granules.

The pharmacological action of the MAG expression promoter of the present invention is explained in the following by referring to Experimental Examples.

Experimental Example 1

The preparation of nerve cell followed the method of Seung U. Kim (Experimental Protocols for Brain and Nerve—From cultured cell to functional analysis, ed. Katsuhiko Mikoshiba, Takao Shimizu, Yodosha). That is, an embryo was taken out from a 18-day pregnant female rat (Crj: CD(SD)IGS), from which dorsal spinal nerve root ganglia (hereinafter to be referred to as DRG) was removed under a stereoscopic microscope. DRG was treated with 0.25% trypsin and DNase I at 37° C. to disperse the cells. Adherent cells other than nerve cells were removed and the cells (5000 cells) were plated on a polylysine-coated plate. The cells were cultured in DMEM containing 10% FCS supplemented with the nerve growth factor (hereinafter to be referred to as NGF, 50 ng/ml) in a $CO_2$ incubator. After 3 days of culture, the medium was changed to one containing Ara-C (1 μmol/l) to remove proliferative cells other than the nerve cells.

The preparation of Schwann cells followed the method of Ichiro Matsuoka (Springer Neuroscience Lab Manual 1, ed. Hiroshi Hatanaka, Springer-Verlag Tokyo). That is, the sciatic nerve of a neonatal rat (1 to 3 days postnatal, (Crj: CD(SD)IGS)) was removed under a stereoscopic microscope and adventitia was removed. By treating with trypsin/collagenase and DNase I in CMF-HBSS, the cells were dispersed. Using a culture flask, the cells were cultured in DMEM containing 10% FCS in a $CO_2$ incubator. After culturing in a medium containing Ara-C, the cells were recovered and the cell suspension was treated successively with anti-Thy 1.1 and rabbit complement to remove cells other than the Schwann cells. Using a collagen-coated culture flask, the cells were cultured in DMEM containing 10% FCS in a $CO_2$ incubator.

After 1 week from the start of the culture of DRG nerve cells, Schwann cells (20,000 cells) were plated on a plate in which DRG nerve cells had been cultured. The medium for co-culture was DMEM containing 2 μmol/l of forskolin, 50 ng/ml of NGF and 10% FCS. The next day, after attachment of the Schwann cells, the compound of the present invention (the above-mentioned Y-128, 3 μmol/l) dissolved in dimethyl sulfoxide (DMSO), or, as a positive control compound, ascorbic acid (50 μg/ml) was added every 2 or 3 days. As a negative control compound, the vehicle DMSO was treated in the same manner.

After 2 weeks from the start of the co-culture, myelin was stained according to the method of Eldridge C F et al. (J. Cell Biol., 105, p. 1023–1034 (1987)). That is, the cells were fixed with a 10% neutral buffered formalin solution and preserved at 4° C. overnight. After removal of the formalin solution, the cells were fixed again with 0.1% osmium tetroxide solution for 1 h and stained with Sudan Black B stain for 30 min. A stained sample (12 wells for each group) was observed under a microscope, and one view of the part where axon was most noticeably stained in each well was selected and photographed with a Polaroid camera.

Figure 2:
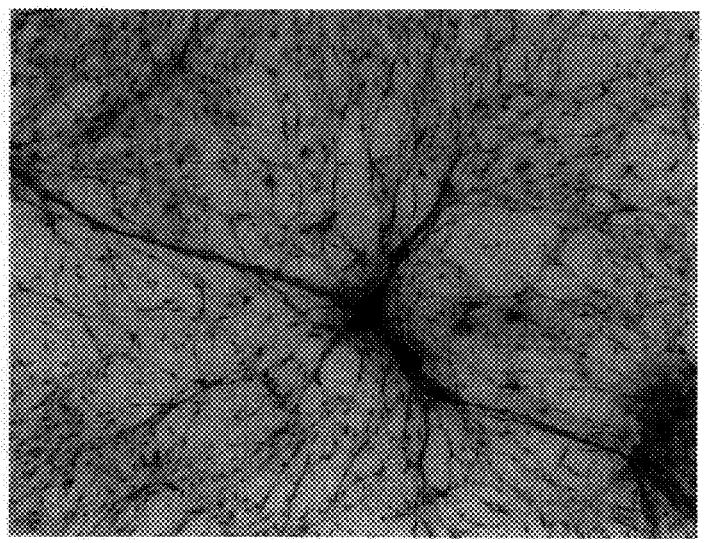
Figure 3:
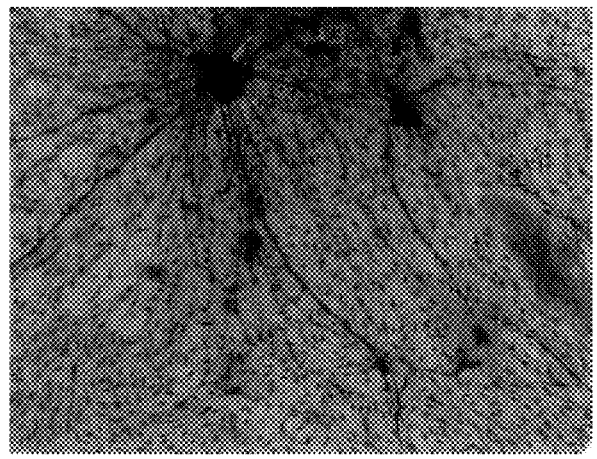

FIG. 1–FIG. 3 show stained axon in each group. In a medium addition group, axon was not stained in any well (see FIG. 1). In an ascorbic acid addition group, axon was stained deep in every well (see FIG. 2). In the compound of the present invention (Y-128) addition group (3 µmol/l), axon was stained as deep as ascorbic acid addition group in 5 wells out of 12 wells (see FIG. 3). From the above-mentioned Experimental Example, it was clarified that the compound of the present invention (Y-128) promoted myelination of axon.

Experimental Example 2

According to the method described in Experimental Example 1, DRG nerve cells and Schwann cells were co-cultured. A DMSO solution containing the compound of the present invention (Y-128, 1, 3, 10 or 30 µmol/l) or ascorbic acid (50 µg/ml) as a positive control compound was added to the medium every 2 days for 2 weeks. As a negative control compound, the vehicle DMSO was added in the same manner. After 2 weeks from the start of the addition of the compound, the medium was removed and a sample buffer containing sodium dodecyl sulfate (SDS) was added to the well for solubilization of the cells.

Figure 4:
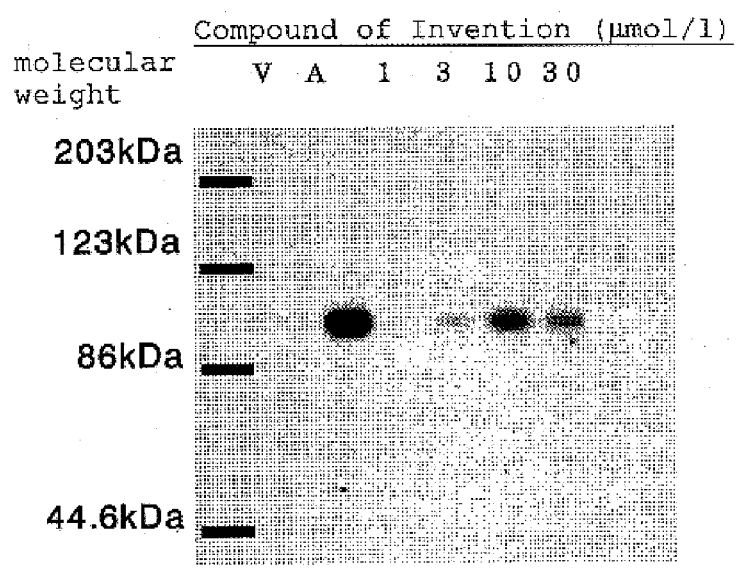
FIG. 4 shows an image of an X ray film obtained by Experimental Example 2, and MAG expression in the cells cultured with the compound of the present invention, the negative control compound or the positive control compound.

A part thereof was separated by polyacrylamide gel electrophoresis and the migrated protein was transferred to a PVDF membrane. By immunoblotting and chemiluminescence, the objective protein was detected on an X ray film. A band detected at about 100 kDa migration was identified as a signal of myelin-related glycoprotein (MAG). The X ray film was scanned and the image was imported to a computer, and the expression of MAG was semi-quantitatively determined using an analysis software, ImageQuaNT (Molecular Dynamics). FIG. 4 shows the MAG expression in the X ray film. From the above-mentioned Experimental Example, it was clarified that the compound of the present invention (Y-128) increased the expression of MAG from the concentration of 3 µmol/l.

Experimental Example 3

Figure 5:
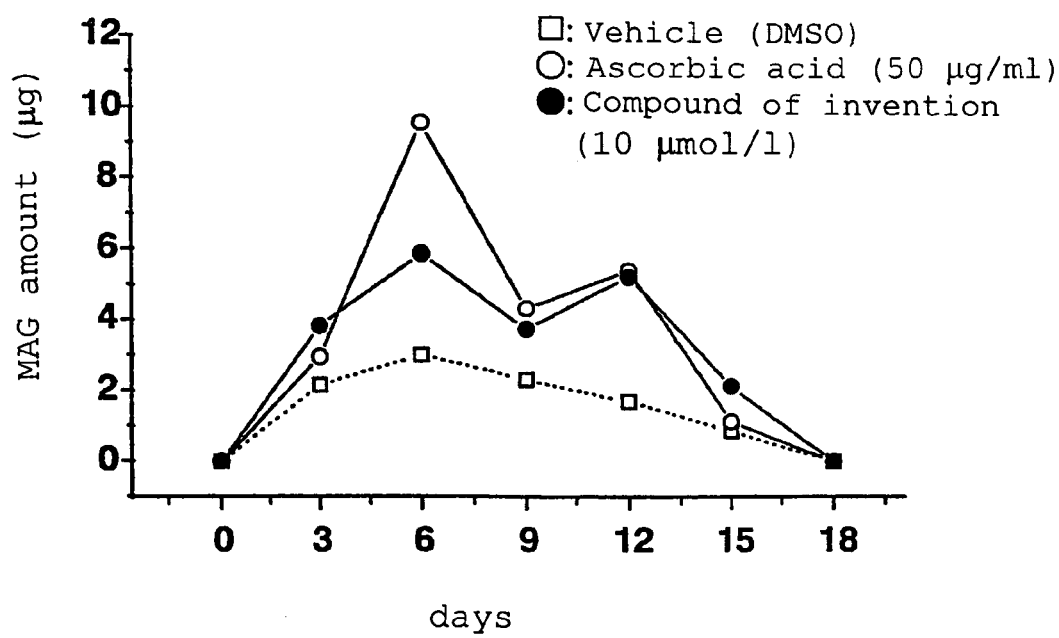
FIG. 5 shows the results of Experimental Example 3, and the time-course changes in the MAG expression in the cells cultured with the compound of the present invention, the negative control compound or the positive control compound.

According to the method described in Experimental Example 1, DRG nerve cells and Schwann cells were co-cultured. A DMSO solution containing the compound of the present invention (Y-128, 10 µmol/ml) or ascorbic acid (50 µg/ml) as a positive control compound was added to the medium every 2 days. The medium DMSO was added in the same manner as was the negative control compound. In the same manner as in Experimental Example 2, MAG was quantitatively determined before addition of the compounds and 3, 6, 9, 12, 15 and 18 days after addition. FIG. 5 shows the results.

From the above-mentioned Experimental Example, it was clarified that the compound of the present invention (Y-128) increased the expression of MAG maximally at 6 days and 12 days after the addition, and 18 days later, the expression of MAG disappeared. The time-course changes of MAG expression by the compound of the present invention (Y-128) was the same as that by the positive control compound, ascorbic acid.

Experimental Example 4

Experimental Allergic Encephalomyelitis (EAE (Experimental Autoimmune Encephalomyelitis))

The myelin basic protein of guinea pig is prepared by extracting the spinal cord homogenate with an acid and allowing precipitation with ammonium sulfate. The myelin basic protein and the same amount of Freund's complete adjuvant (containing 4 mg/ml Mycobacteria H37Ra) are mixed and emulsified. The prepared emulsion (0.1 ml) is injected once to the sole of a hind limb of 8 to 12-week-old female Lewis rat. Y-128 (10 mg/kg) is orally administered once a day for 4 weeks from immediately after EAE induction. After the final administration, the symptom of the rat is scored as follows, based on which the effect is evaluated.

0: no symptom
1: tail hanging down limply
2: paralysis of hind limb
3: paralysis of all limbs
4: on the verge of death
5: death Experimental Example 5

Allergic Neuritis (EAN (Experimental Autoimmune Neuritis))

Protein peptide (100 µg, corresponding to 53–78 of the amino acid sequence of bovine P2 protein) and the same amount of Freund's complete adjuvant (containing 0.5 mg/ml *Mycobacterium tuberculosis*) are mixed and emulsified. The prepared emulsion (0.1 ml) is injected once to the sole of a hind limb of 6 to 8-week-old female Lewis rat. Y-128 (10 mg/kg) is orally administered once a day for 4 weeks from immediately after EAN induction. After the final administration, the symptom of the rat is scored as follows, based on which the effect is evaluated.

0: no symptom
1: tail with weakened force
2: tail hanging down limply
3: disorder in maintaining righting
4: disappearance of righting maintenance
5: ataxic gait
6: mild paralysis of hind limb
7: severe paralysis
8: paralysis of all limbs
9: on the verge of death
10: death

INDUSTRIAL APPLICABILITY

The MAG expression promoter of the present invention is useful as an agent for the prophylaxis and/or treatment of diseases mainly presenting hypomyelination, and further, dysmyelination or demyelination. More particularly, it is useful as an agent for the prophylaxis and/or treatment of diseases of mammals inclusive of humans, such as multiple sclerosis, encephalitis, myelitis, Guillain-Barré syndrome, chronic inflammatory demyelinating polyradiculitis, heavy metal toxicosis, diphtheria toxicosis, hypothyroidism, metachromatic leukodegeneration, Charcot-Marie-Tooth disease and the like.

Afterword

This application is based on a patent application No. 144336/1999 filed in Japan, the contents of which are hereby incorporated by reference. The present invention should not be limited in scope by the specific embodiments described in the specification. Variations and modifications of the present invention will be obvious to those of ordinary skill in the art from the foregoing descriptions. Such variations and modifications are intended to be within the scope of the present invention. Any disclosures by various publications and the like cited herein are hereby incorporated in its entirety into the present invention by reference thereto.

What is claimed is:

1. A method for promoting a myelination of axon, which method comprises administering 4-[α-hydroxy-5-(1-imidazolyl)-2-methylbenzyl]-3,5-dimethylbenzoic acid, an optically active form thereof or a pharmaceutically acceptable salt thereof to a mammal afflicted with a disease selected from the group consisting of multiple sclerosis, encephalitis, myelitis, Guillain-Barre' syndrome, chronic inflammatory demyelinating polyradiculitis, heavy metal toxicosis, diphtheria toxicosis, Hypothyroidism, metachromatic leukodegeneration and Charcot-Marie-Tooth disease.

2. The method of claim 1, wherein the mammal is a human.

* * * * *